United States Patent
Coss

(10) Patent No.: US 6,602,229 B2
(45) Date of Patent: Aug. 5, 2003

(54) VIBRATING INJECTION NEEDLE

(76) Inventor: Ronald G. Coss, 3 Overlook Dr., Newport Coast, CA (US) 92657

( * ) Notice: Subject to any disclaimer, the term of this patent is extended or adjusted under 35 U.S.C. 154(b) by 0 days.

(21) Appl. No.: 09/939,354

(22) Filed: Aug. 24, 2001

(65) Prior Publication Data

US 2003/0040714 A1 Feb. 27, 2003

(51) Int. Cl.⁷ .......................... A61B 17/20; A61M 5/00
(52) U.S. Cl. ........................................ 604/187; 604/22
(58) Field of Search ................................ 604/115, 117, 604/188, 272, 204, 239–243, 187, 131, 22; 606/147, 148; 128/DIG. 1; 141/330, 375, 329, 328

(56) References Cited

U.S. PATENT DOCUMENTS

| | | | |
|---|---|---|---|
| 2,258,857 A | | 10/1941 | McCann |
| 2,525,398 A | | 10/1950 | Collins |
| 3,308,823 A | | 3/1967 | Peterson |
| 3,620,209 A | | 11/1971 | Kravitz |
| 5,279,552 A | * | 1/1994 | Magnet ........................ 604/47 |
| 5,647,851 A | * | 7/1997 | Pokras ........................ 604/131 |
| 5,902,279 A | | 5/1999 | Powles et al. |
| 6,033,421 A | * | 3/2000 | Theiss et al. ................ 606/186 |

FOREIGN PATENT DOCUMENTS

| | | | | |
|---|---|---|---|---|
| DE | 100 04 496 A1 | 8/2000 | ............ | A61M/5/20 |
| EP | 0 302 278 A1 | 2/1989 | ............ | A61M/5/20 |
| JP | 09239031 | 9/1997 | ............ | A61M/5/32 |
| WO | WO 00/18305 | 4/2000 | ............ | A61B/17/32 |

* cited by examiner

Primary Examiner—Brian L. Casler
Assistant Examiner—Matthew DeSanto
(74) Attorney, Agent, or Firm—Knobbe, Martens, Olson & Bear, LLP

(57) ABSTRACT

A portable battery-powered vibrating motor that can be clipped on any standard syringe provides vibration to a needle to be inserted into a patient to minimize discomfort. The clip is releasably attached to the syringe, and a holder connected to the clip releasably receives the motor. This enables the motor to be used on other units and enables the syringe and the clip to be sterilized, without the motor.

13 Claims, 4 Drawing Sheets

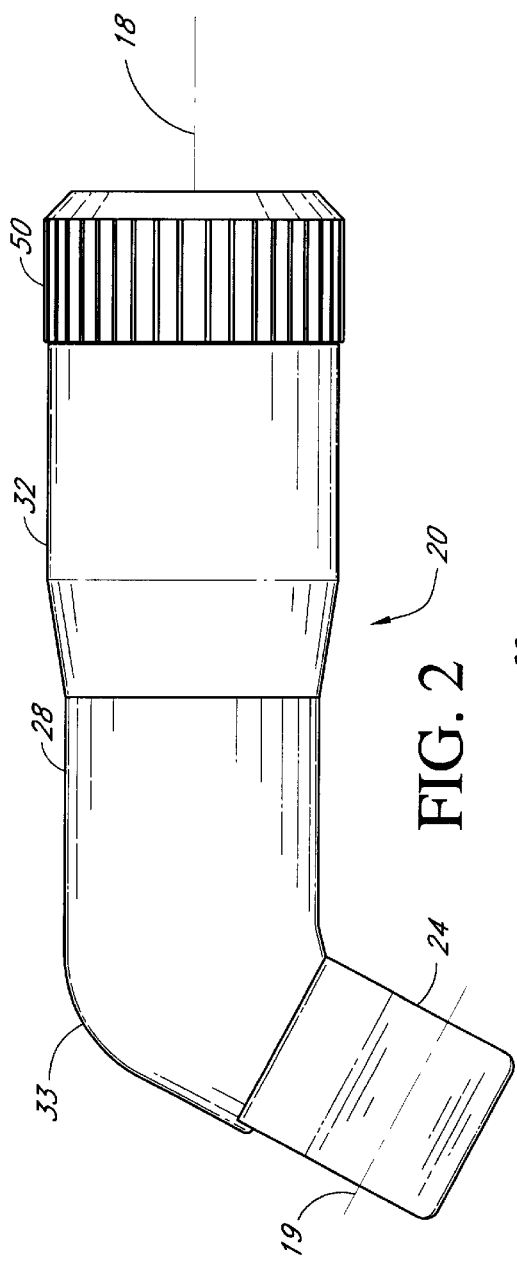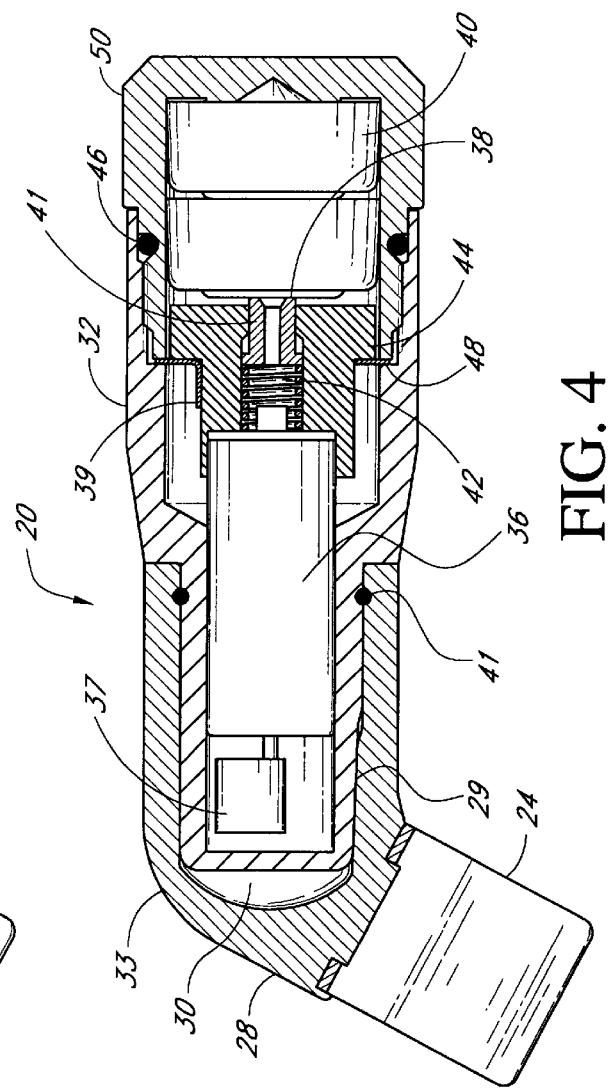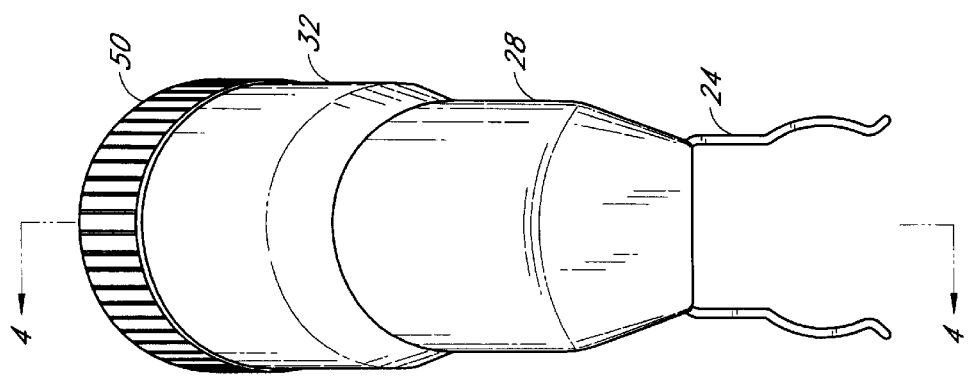

FIG. 5A
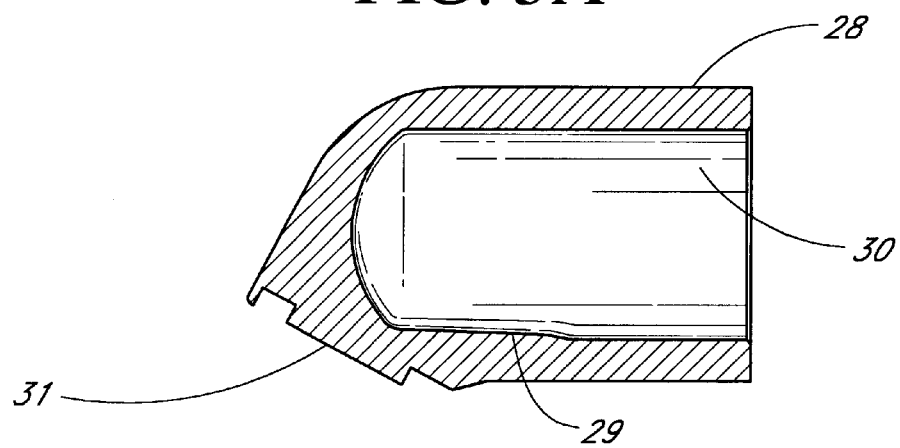
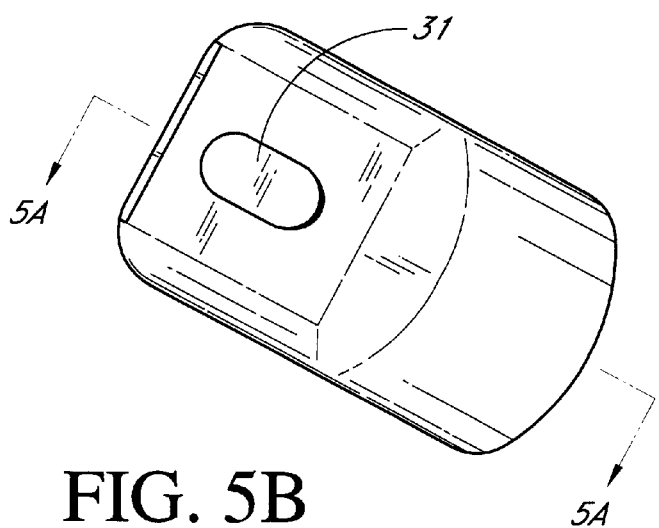
FIG. 5B

VIBRATING INJECTION NEEDLE

BACKGROUND OF THE INVENTION

1. Field of the Invention

The present invention relates to devices for administering medicinal fluids to patients and, more particularly, to a device for vibrating a syringe needle during the administration of medication to a patient.

2. Description of the Related Art

Medication is administered to patients in many different medical and dental procedures. They can be administered in a variety of different ways, such as orally, by inhalation, or by injection through a needle. Injections are in many cases the preferred means of delivery due to the short time lapse between the injection of the medication and the resulting benefit to the patient. The benefit can be realized almost instantly because the medication can be injected directly to the desired area, or may be directly injected intravenously into the patient's bloodstream. By contrast with medication taken orally, there is typically a substantial delay while the ingested medication is fully digested and delivered to the desired site within the patient's body.

It has been common practice in the medical field, both in injecting anesthetic to a patient's gums or in penetrating the skin or a vein, to utilize a conventional syringe incorporating a metallic needle. In the case of injecting an anesthetic in, for instance, a patient's gum, the dentist will typically apply a topical anesthetic to the surface of the gum; and then, possibly while endeavoring to conceal the syringe from view by the patient, approach the gum site with the point of the needle. The needle is typically then forced through the gum surface tissue. Different medical technicians employ different procedures for this application, all designed to minimize trauma and pain to the patient. However, all such techniques still involve popping the needle point through the gum skin, an area that typically has highly sensitive nerves. Consequently, the patient often is exposed to considerable pain during this entry procedure. After subcutaneous entry, the needle point is maneuvered to the desired location for application of the anesthetic. The plunger is then typically depressed under the force of the dentist's thumb to force the medication through the lumen of the needle to be forced into the gum tissue for the purpose of anesthetizing the site. It has been shown that a great deal of pain may be experienced after subcutaneous entry and during forced injection of the anesthetic into the gum tissue. It is understood that the anesthetic forced from the tip of the needle tends to pool near the tip of the needle creating somewhat of a balloon effect within the tissue. The volume of anesthetic so ballooned at this site is then slowly absorbed into the surrounding tissue to slowly reduce such balloon effect.

Because of the associated pain and discomfort caused by piercing of the skin by the needle and by forcing medication into the tissue, injection remains to be one of the least preferred methods for receiving medication, from the patients' perspective. Especially when the injection is being made in particularly sensitive places such as the roof of the mouth in dentistry injections, there can be immense amounts of pain involved. As a result of being subjected over the years to many such painful and uncomfortable injections, many patients harbor a fear of, and apprehension toward, such injections. Some patients refuse to receive injections, while others simply delay, or altogether avoid, seeking medical or dental attention rather than face the possibility of being subjected to an injection A device that was proposed in an attempt to reduce the pain and discomfort associated with injections, as cited in U.S. Pat. No. 2,258,857 by McCann, includes a vibrating contact element for placement against the skin of the patient adjacent the area to receive the injection. Vibration of the contact element against the patient's skin purportedly serves to distract and confuse the patient's nerve functions, thus relieving the pain normally experienced during an injection. This device is not free from shortcomings however. The device is bulky and cumbersome, requiring two hands to maintain the contact element pressed against the patient's skin while actuating the vibration means to vibrate such contact element. Thus, either an assistant is required to handle the device while the doctor or dentist performs the injection, or the patient must handle the device himself or herself. In addition, the device provides no vibration to the needle itself. As such, it only serves to act upon the surface skin thereby limiting the effectiveness for injections penetrating deeper below the skin.

Another device proposed in U.S. Pat. No. 5,647,851 by Pokras employs a vibrating device which houses a syringe, needle, and all the necessary parts of the vibrator in a single, hand-held unit. Unfortunately, this device is difficult to manufacture due to its complex design, and requires greater amounts of effort in the processes of exchanging needles, sterilizing, replacing parts, etc.

As such, it may be appreciated that there continues to be a need for a vibrating syringe device that is effective in reducing the pain and discomfort associated with injections, as well as convenient to use and maintain.

SUMMARY OF THE INVENTION

The present invention overcomes the above problems in the art by providing a portable, preferably battery-powered, vibrating motor assembly which can be clipped on any syringe and needle assembly to provide vibration to the needle during operation on a patient. The vibrating motor assembly generally comprises a tubular shaped housing formed with an interior compartment, coupled with a clip for attachment to a syringe barrel. The interior compartment of the housing preferably holds a battery powered motor including an eccentrically weighted shaft, which serves to supply vibration to the entire assembly and thus to the needle during operation of the motor. The operator may easily activate the vibrator as the needle is advanced to penetrate the patient's body, to reduce the amount of pain and discomfort which would otherwise be experienced.

Advantageously, this device allows the user to easily remove the motor portion of the assembly, without also having to remove the clip from the syringe. This makes it easier for the user to sterilize the syringe and the clip portion, which may become contaminated during operation, without having to also sterilize the vibrating motor.

Furthermore, it allows the user to keep the clip portions and the syringes attached to one another at all times, so that only the motor portion must be attached or removed. Alternatively, the clip may be kept connected and removed as a unit.

BRIEF DESCRIPTION OF THE DRAWINGS

FIG. 2 shows a side view of the vibrator assembly of FIG. 1.

FIG. 3 shows a front view of the vibrator assembly.

FIG. 4 shows a side cross-sectional view of a vibrator assembly.

FIG. 5A shows a side cross-sectional view of the vibrator housing.

FIG. 5B shows a bottom view of the vibrator housing.

DETAILED DESCRIPTION OF THE PREFERRED EMBODIMENT

Figure 1:
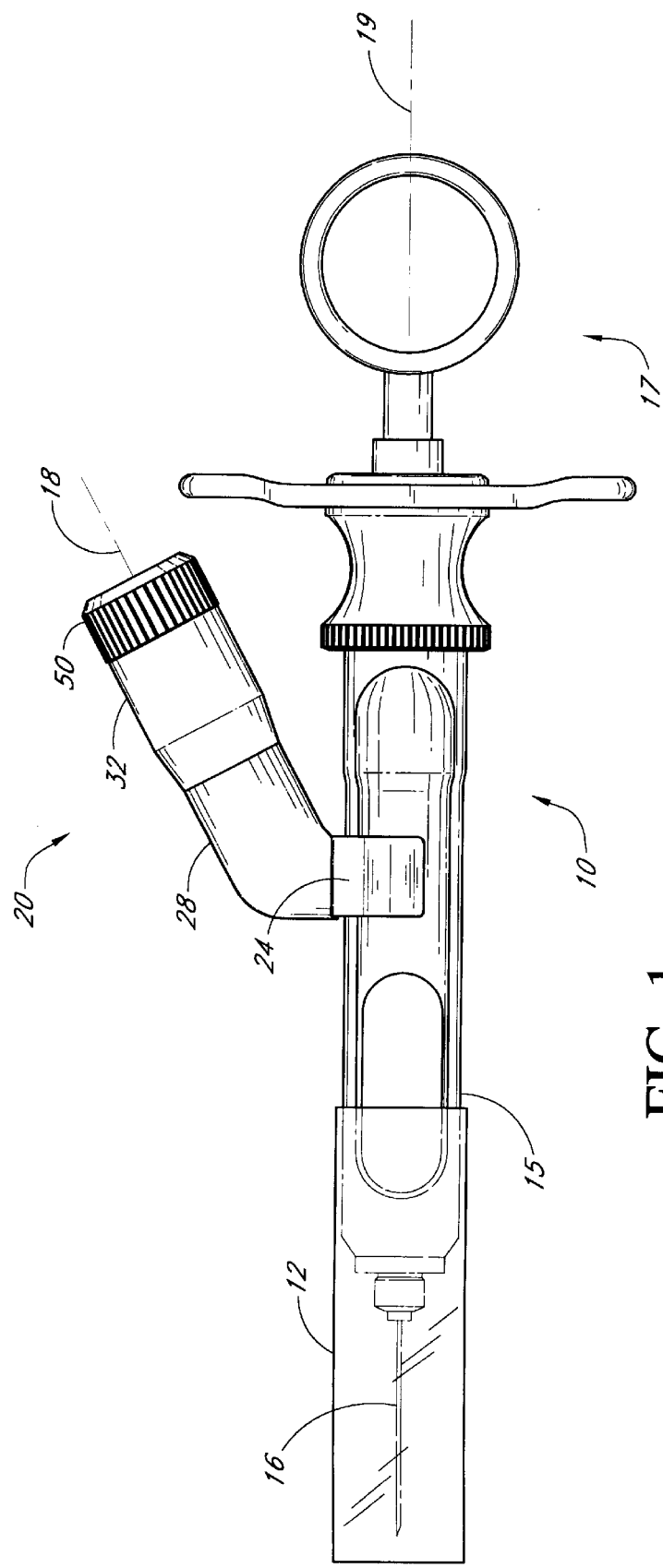
FIG. 1 shows a side view of a vibrator assembly attached to a syringe.

Referring now to FIG. 1, one exemplary embodiment of the vibration injection needle 10 shows a needle-holding device such as a syringe 15 having a vibrator assembly 20 attached thereto. The syringe is of a type well known in the art, having a sharply pointed needle 16 at its distal end for penetration of a patient's skin, and a plunger 17 at its proximal end for delivery of medication through the needle. A protective sheath 12 may cover the distal end of the syringe and the needle when it is not in use, but may be retracted during operation. The vibrator assembly 20 is attached to the syringe via a connector in the form of a clip 24, and further comprises a vibrator housing 28, a motor housing 32 and a control knob 50.

As seen in FIGS. 2–4, the clip 24 is affixed to the vibrator housing 28 which has a socket 30 in which the motor housing 32 is received. The vibrator housing 28 includes an elbow 33 that creates an angle between an axis 18 of the socket 30 and the syringe axis 19. The angle is approximately 30° but may be any angle which is small enough to keep the entire assembly close to the syringe but large enough so that it does not get in the way of the operator's hands.

Referring to FIG. 4, the motor housing is a generally cylindrically shaped tube having one end closed and one end open to snugly receive a motor 36 having an eccentrically weighted shaft 37 on its inner end. The outer end of the motor 36 mates with an annular insulator 44 enclosing a spring 42 and a battery contact 38. A contact ring 48 surrounds the insulator 44 which has a tab 39 connected to a motor wire or terminal (not shown). The ring 48 thus can contact the control knob 50 to provide a conductive path to the negative side of one of the two batteries 40. Another terminal or wire (not shown) of the motor 36 is connected to the battery contact 38 which is urged by the spring 42 into contact with the positive side of the battery 40. As seen, the cup-shaped knob encloses the battery and the open end of the knob threads into the open end of the motor housing 32. An O-ring 46 fits between the inner surface of the open end of the motor housing in the outer surface of the control knob to create a tighter fit and to prevent water leakage to the cavity in the motor housing.

The clip 24 and the vibrator housing 28 form a coupler for releasably receiving the motor housing 32. The motor housing 32 may be frictionally held in the socket of the vibrator housing 28; however, it is preferably held more positively by an O-ring 41 or other retainer positioned in a suitable groove between the exterior of the housing 32 and the wall of the socket 30 in the vibrator housing. The housing 32, which is shown in more detail in FIGS. 5A and 5B, and the wall of the socket 30 are provided with structure, such as flat areas 29, to prevent relative rotation when the knob 50 is rotated.

Figure 6B:
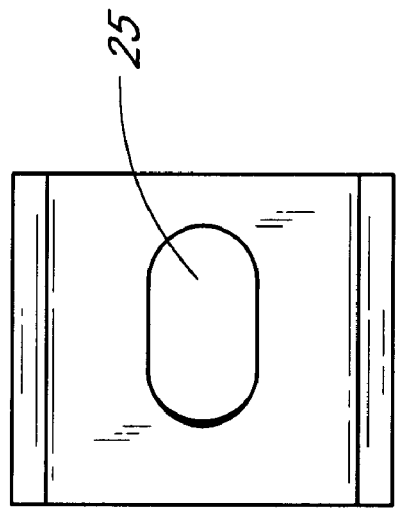
FIG. 6B shows a bottom view of the clip.
Figure 6A:
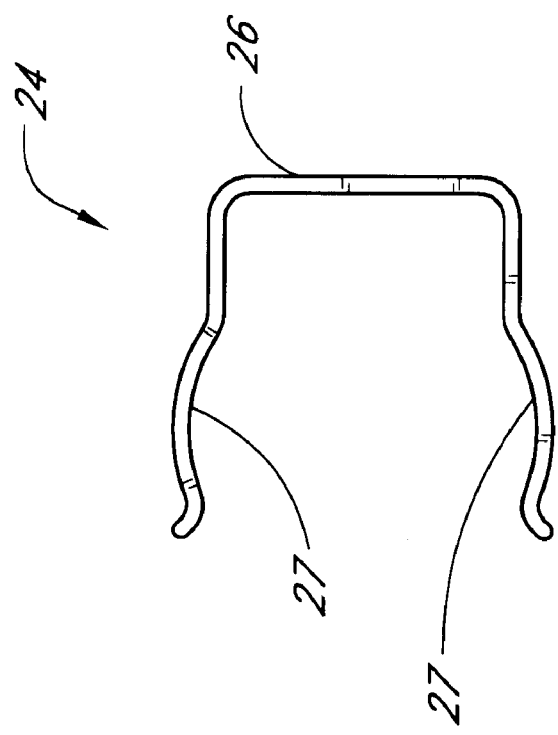
FIG. 6A shows a front view of the clip of FIG. 1.

On the closed end of the vibrator housing is a flat surface having a protrusion 31 which cooperates with the hole 25 in the clip 24. The clip 24, shown in FIGS. 6A and 6B comprises a flat back wall 26 and two flexible legs 27 which are curved to grip the tubular shape of the syringe, and are flexible enough to spread and fit on the syringe barrel and then grip different size syringes. The clip of course can be of whatever size is desired. The clip 24 is affixed to the vibrator housing 28 by the protrusion extending through the hole 25 and joining the two pieces by suitable means, such as sonic welding.

To more fully explain how the components of the vibrator work electrically, refer to FIG. 4. The battery contact 38 pushed by the spring 42 is constantly creating an electrical pathway between one terminal of the motor and the battery. The contact ring 48 engages the edge of the control knob 50, the interior of which forms an electrical pathway to the negative side of the batteries 40 when the knob is fully closed. When the knob 50 is unthreaded, it separates from the ring 48, thus ceasing electrical power to the motor 36.

There are several benefits to the described arrangement. The clip allows the assembly to be mounted on syringes without coordination with syringe manufacturers, and it can accommodate variations in the diameter of syringe housings. As mentioned briefly above, the angle of the vibrator housing keeps the unit close to the syringe to enhance transmission of the vibration, while not interfering with operation of the syringe. The clip 24 can be retracted if there is the sheath 12 to be retracted to uncover the needle, but yet the clip will adequately transmit vibration to the syringe housing no matter where located on the housing.

Another primary advantage to this device is that the actual vibrating piece (the motor housing 32) can be separated easily from the vibrator housing and clip assembly. This allows the vibrator housing and the clip to remain attached to the syringe, while the vibrator may be withdrawn. Thus, one motor may be used with many syringes. When an injection is to be made, the operator would then only need to slide the motor housing into the cavity of the vibrator housing and rotate the knob to energize the motor. This provides a further advantage when the contaminated components of the assembly need to be sterilized after use on a patient. Because only the components that were in direct contact or close to the patient need to be sterilized, the motor housing can be easily removed from the rest of the assembly which can then be subjected to high temperature sterilization in an autoclave. However, with the clip positioned to the rear of the syringe, it may not be necessary to sterilize the clip or the vibrator housing. In view of that, the two housings could be permanently connected, or a clip could be mounted directly on the motor housing.

While the invention disclosed herein has been described by means of specific embodiments and applications thereof, numerous modifications and variations could be made thereto by those skilled in the art without departing from the scope of the invention as set forth in the claims. For example, the vibrator may be releasably coupled to a syringe by means other than the particular clip illustrated so long as the vibration is adequately transmitted to the needle.

What is claimed is:

1. An assembly to minimize pain to a patient when a needle is inserted into the patient, comprising:
   a vibrator including a housing; and
   a clip having a pair of spaced flexible legs joined by an end wall, which is fixed to said housing in a manner to cause the clip to vibrate, the clip legs being configured to spread and to releasably mount the vibrator directly on a syringe housing in a manner to support the vibrator on the syringe and to cause the syringe and a needle rigidly held by the syringe to vibrate as the needle is inserted into the patient.

2. The assembly of claim 1, wherein said vibrator housing includes a socket joined to said clip wall and sized to removably receive a vibrator motor within said socket.

3. The assembly of claim 2, wherein said vibrator includes a motor having an eccentrically weighted shaft that vibrates the vibrator housing, the syringe and the needle when the motor is mounted in said socket.

4. The assembly of claim 1, wherein said syringe has a generally cylindrical housing, and wherein said socket is generally cylindrical and is oriented at an acute angle with respect to said syringe housing so that the vibrator extends away from the syringe housing and the needle so as not to interfere with operation of the syringe.

5. The assembly of claim 1, including the syringe housing.

6. The assembly of claim 5, wherein said syringe has a housing for holding a capsule of liquid to be injected into a patient, and said clip legs clip on said housing.

7. The assembly of claim 1, wherein said clip is made of material that can be sterilized in an autoclave with the needle holding device.

8. The assembly of claim 1, wherein said vibrator is releasably coupled to said clip so that the vibrator can be readily coupled to clips connected to other syringes.

9. An apparatus comprising
a syringe having a generally cylindrical housing for receiving a capsule of liquid to be injected into a patient, said syringe having a needle fixed on one end, and a plunger on an opposite end for forcing the liquid through the needle into the patient;
a vibrator including a housing;
a clip mounted on an end of the vibrator housing in a manner to cause the clip to vibrate, said clip having a pair of spring legs that enable the clip and the vibrator to be removably fixed to and supported solely by the syringe housing in a manner to cause the vibration from the vibrator to be transmitted through the clip directly to the syringe housing so as to cause the syringe housing and the needle to vibrate.

10. The apparatus of claim 9, including a socket in said vibrator housing sized to removably receive the vibrator.

11. The apparatus of claim 10, wherein said vibrator includes an electric motor confined within a motor housing with the forward end of the motor housing being sized to snugly and removably fit within said socket so as to enable the motor together with the motor housing to be interchangeably utilized with one or more vibrator housing and clip combination mounted on one or more syringes and to permit the clip and the vibrator housing to be separated from the motor housing for sterilization of the clip and the vibrator housing.

12. The apparatus of claim 11 wherein said vibrator includes a battery and switch for energizing said motor with the battery and switch being located in an open end of said motor housing opposite from the motor housing end which fits within the vibrator housing; and a cap closing said motor housing open end, said cap being movable to operate such switch to energize said motor.

13. The apparatus of claim 10 wherein said clip legs are fixed to the vibrator housing so that when the clip is mounted on the syringe housing, the vibrator housing extends away from the syringe housing at an acute angle with an open end of the socket extending towards the plunger end of the syringe.

* * * * *